(12) United States Patent
Yuki et al.

(10) Patent No.: US 7,652,017 B2
(45) Date of Patent: Jan. 26, 2010

(54) REMEDIES AND/OR PREVENTIVES FOR NERVOUS SYSTEM DISORDERS

(75) Inventors: Satoshi Yuki, Tokyo (JP); Naruhiko Yoshii, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 310 days.

(21) Appl. No.: 10/168,342

(22) PCT Filed: Dec. 20, 2000

(86) PCT No.: PCT/JP00/09024

§ 371 (c)(1),
(2), (4) Date: Sep. 6, 2002

(87) PCT Pub. No.: WO01/45739

PCT Pub. Date: Jun. 28, 2001

(65) Prior Publication Data

US 2003/0114427 A1    Jun. 19, 2003

(30) Foreign Application Priority Data

Dec. 21, 1999    (JP)    ................................. 11/362680
Mar. 9, 2000     (JP)    ............................. 2000-065272

(51) Int. Cl.
*A61K 31/496*   (2006.01)
*A01N 43/62*    (2006.01)

(52) U.S. Cl. ................. 514/255.01; 514/218

(58) Field of Classification Search ............ 514/252.12, 514/255.03, 255.01, 218
See application file for complete search history.

(56) References Cited

U.S. PATENT DOCUMENTS 4,789,675 A * 12/1988 Meguro et al. ........... 514/229.8
5,053,409 A * 10/1991 Okushima et al. ...... 514/255.03
5,990,113 A * 11/1999 Yamazaki et al. ...... 514/255.03

FOREIGN PATENT DOCUMENTS

JP    3-7263     1/1991
WO   94/13291    6/1994
WO   94/14786    7/1994

OTHER PUBLICATIONS

Beers, M.H. and Berkow, R., Editors-in-Chief, The Merck Manual of Diagnosis and Therapy, 17th Edition, pp. 1418-1427 and 1668-1681, 1999.*
Parsons et al. J. of NeuroChemistry 68 (3) 1124-1134.*

* cited by examiner

*Primary Examiner*—Michael G Hartley
*Assistant Examiner*—Shirley V Gembeh
(74) *Attorney, Agent, or Firm*—Wenderoth, Lind & Ponack, L.L.P.

(57) ABSTRACT

A therapeutic and/or prophylactic agent for nervous system disorder comprising as the active ingredient substances having an effect of improving calcium ion uptake of cardiac sarcoplasmic reticulum and/or an effect of inhibiting overaccumulation of intracellular calcium ions is offered. Preferably, the therapeutic and/or prophylactic agent for disease selected from the group consisting of cerebrovascular disease, traumatic head injury and postencephalitis and the therapeutic and/or prophylactic agent for disease selected from the group consisting of dementia and neuronal degeneration disease are offered.

2 Claims, 8 Drawing Sheets

Results are shown as Mean Value + Standard Error
*P < 0.05; **P < 0.01 v.s. Control Group
(After repeated two-way ANOVA, determined by comparison using t-test)

FIG. 7

Postischemic Region

Results are shown as Mean Value + Standard Error
*P < 0.05 (repeated ANOVA)

FIG. 8

Non-Ischemic Region

Results are shown as Mean Value + Standard Error
N.S. No significant difference (repeated ANOVA)

REMEDIES AND/OR PREVENTIVES FOR NERVOUS SYSTEM DISORDERS

This application is a 371 of PCT/JP00/09024 filed Dec. 20, 2000.

FIELD OF THE INVENTION

The present invention relates to a therapeutic and/or prophylactic agent for nervous system disorder which comprises as the active ingredient substances having an effect of improving calcium ion uptake of cardiac sarcoplasmic reticulum and/or an effect of inhibiting overaccumulation of intracellular calcium ions.

BACKGROUND OF THE INVENTION

Statistics on causes of death and rates of hospitalization and treatment in the world show that cerebrovascular diseases always rank high. In particular ischemic cerebrovascular diseases are recently increasing as compared with hemorrhagic cerebrovascular diseases. An ischemic cerebrovascular disease is choking of the cerebral blood flow by some causes, ultimately resulting in necrosis of the cerebral tissue. Inter alia, neuronal cells are vulnerable and therefore ready to die on occurrence of ischemia. Neuronal cell death due to ischemia is known to be the most common condition leading to falling off of nerves due to cerebral disturbance (see Shinkei Shinpo, Vol. 36(2), pp. 225-235 (1992) and Dementia, Vol. 7, pp. 161-171 (1993). Hence, a substance which prevents neuronal cell death is believed to create a therapeutic and prophylactic agent effective on cerebrovascular disease. However, such an agent having sufficient efficacy has not yet been found.

It is known that similar neuronal cell death also accompanies traumatic head injury and postencephalitis (see J. Neurosurq., Vol. 67, pp. 110-119 (1987), Shinken Shinpo, Vol. 35(5), pp. 705-716 (1991), and Taisha, Vol. 26, pp. 253-257 (1989)). Accordingly, prevention of neuronal cell death is considered to be treatment and prevention effective on these diseases Recently, dementia has been recognized as social problem with the increase of aging society. Dementia is classified types of pathology as dementia of Alzheimer type or dementia of cerebrovascular type. Both of them accompany clinically disturbance of intelligence as basic manifestation (amnesia, disturbance of memorization, disorientation, fugue, etc.) and delirium including phantasm and hallucination, delusion, aggressive behavior, strain, agitation or hypobulia as manifestation caused by disturbance of intelligence. For the purpose of improving the manifestation caused by dementia, agents for improving brain metabolism and agents for improving cerebral circulation have been put to practical use. However, the efficacy is not enough because the above agents are not effective for disturbance of intelligence as basic manifestation of dementia and development of more effective medicaments has been waited.

On the other hand, it is known that the aminobenzensulfonic acid derivatives being represented by the following formula (I):

(I)

(wherein $R_1$ represents hydrogen atom, $C_1$-$C_6$ alkyl group, $C_3$-$C_7$ cycloalkyl group, $C_1$-$C_4$ halogenated alkyl group, halogen atom or $C_6$-$C_{12}$ aryl group, $R_2$ represents hydrogen atom, $C_1$-$C_6$ alkyl group, or $C_7$-$C_{12}$ aralkyl group which may also have at least one substituent selected from the group consisting of cyano groups, nitro groups, $C_1$-$C_6$ alkoxy groups, halogen atoms, $C_1$-$C_6$ alkyl groups and amino groups, and n represents an integer of 1 to 4) have an effect of inhibiting overaccumulation of intracellular calcium ions (Japanese Patent Application Publication Nos. 7263/1991, 139127/1992, 221479/1997 and 298077/1998, European Patent Application Publication Nos. 390654 and 779283, and U.S. Pat. Nos. 5,053,409 and 5,990,113) and an effect of improving calcium ion uptake of cardiac sarcoplasmic reticulum (International Patent Application Publication No. WO 99/40919).

It has been disclosed that such compounds may be useful for prevention or treatment of ischemic heart diseases such as myocardial infarction and angina, heart failure, hypertension and arrhythmia. However, any of these publications neither suggested nor stated that these compounds may be useful for prevention or treatment of nervous system disorder.

DISCLOSURE OF THE INVENTION

The present inventors found, after intense studies to develop an effective medicament for nervous system disorder, that the substances having an effect of improving calcium ion uptake of cardiac sarcoplasmic reticulum and/or an effect of inhibiting overaccumulation of intracellular calcium ions shown in the following examples have an effect of inhibiting neuronal cell death, inhibiting neuronal degeneration and improving disorder of memory. The present invention is based on these findings.

In summary, the present invention relates to a therapeutic and/or prophylactic agent for nervous system disorder which comprises as the active ingredient substances having an effect of improving calcium ion uptake of cardiac sarcoplasmic reticulum and/or an effect of inhibiting overaccumulation of intracellular calcium ions.

Preferable embodiments of the present invention include that the substances have an effect of improving calcium ion uptake of cardiac sarcoplasmic reticulum; the substances have an effect of improving calcium ion uptake of cardiac sarcoplasmic reticulum and an effect of inhibiting overaccumulation of intracellular calcium ions; the substances have an effect of improving of the reduced sarcoplasmic reticulum calcium-pumping ATPase activity in brief-ischemic/reperfused myocardium in dogs; the substances have an effect of inhibiting the action of isoproterenol; and the substance is an aminobenzenesulfonic acid derivative or its salt, or hydrate or solvate thereof, the aminobenzenesulfonic acid derivative being represented by the following formula (I):

(I)

(wherein $R_1$ represents hydrogen atom, $C_1$-$C_6$ alkyl group, $C_3$-$C_7$ cycloalkyl group, $C_1$-$C_4$ halogenated alkyl group, halogen atom or $C_6$-$C_{12}$ aryl group, $R_2$ represents hydrogen atom, $C_1$-$C_6$ alkyl group, or $C_7$-$C_{12}$ aralkyl group which may also have at least one substituent selected from the group consisting of cyano groups, nitro groups, $C_1$-$C_6$ alkoxy groups, halogen atoms, $C_1$-$C_6$ alkyl groups and amino groups, and n represents an integer of 1 to 4).

Alternatively, preferable embodiments of the present invention include that the nervous system disorder is selected from the group consisting of cerebrovascular disease, traumatic head injury and postencephalitis; cerebrovascular disease is ischemic cerebrovascular disease; ischemic cerebrovascular disease is selected from the group consisting of stroke, subarachnoid hemorrhage, cerebral hemorrhage and cerebral arterial sclerosis; nervous system disorder is selected from the group consisting of dementia and neuronal degeneration disease; dementia is manifested by the symptom selected from the group consisting of disturbance of intelligence and the symptom caused by disturbance of intelligence; disturbance of intelligence and the symptom caused by disturbance of intelligence are the symptoms selected from the group consisting of amnesia, disturbance of memorization, disorientation, fugue, aprosexia, logopathy, hypobulia, disorder of emotion, delirium, delusion and behavior disorder; and neuronal degeneration disease is selected from the group consisting of Alzheimer's disease, Parkinson's disease, Parkinsonian syndrome, progressive supranuclear pals, subacute sclerosing parencephalitis, Pic's syndrome, corticobasal ganglia degeneration disease, front temporal dementia and disturbance of consciousness or dyskinesia caused by head injury.

Another embodiments of the present invention include that an inhibitor of neuronal cell death which comprises as the active ingredient substances having an effect of improving calcium ion uptake of cardiac sarcoplasmic reticulum and/or an effect of inhibiting overaccumulation of intracellular calcium ions; a protective and/or improving agent for cerebral function which comprises as the active ingredient substances having an effect of improving calcium ion uptake of cardiac sarcoplasmic reticulum and/or an effect of inhibiting overaccumulation of intracellular calcium ions; an inhibitor for neuronal degeneration which comprises as the active ingredient substances having an effect of improving calcium ion uptake of cardiac sarcoplasmic reticulum and/or an effect of inhibiting overaccumulation of intracellular calcium ions; and an improving agent for disorder for memory which comprises as the active ingredient substances having an effect of improving calcium ion uptake of cardiac sarcoplasmic reticulum and/or an effect of inhibiting overaccumulation of intracellular calcium ions.

Alternatively, another embodiments of the present invention include that a method of treating and/or preventing nervous system disorder which comprises as the active ingredient substances having an effect of improving calcium ion uptake of cardiac sarcoplasmic reticulum and/or an effect of inhibiting overaccumulation of intracellular calcium ions; a method of inhibiting neuronal cell death which comprises as the active ingredient substances having an effect of improving calcium ion uptake of cardiac sarcoplasmic reticulum and/or an effect of inhibiting overaccumulation of intracellular calcium ions; a method protecting and/or improving cerebral function which comprises as the active ingredient substances having an effect of improving calcium ion uptake of cardiac sarcoplasmic reticulum and/or an effect of inhibiting overaccumulation of intracellular calcium ions; a method of inhibiting neuronal degeneration which comprises as the active ingredient substances having an effect of improving calcium ion uptake of cardiac sarcoplasmic reticulum and/or an effect of inhibiting overaccumulation of intracellular calcium ions; and a method of improving disorder of memory which comprises as the active ingredient substances having an effect of improving calcium ion uptake of cardiac sarcoplasmic reticulum and/or an effect of inhibiting overaccumulation of intracellular calcium ions.

BEST MODES FOR CARRYING OUT THE INVENTION

The present invention will be described below in detailed.

A therapeutic and/or prophylactic agent for nervous system disorder of the present invention comprises as the active ingredient substances having an effect of improving calcium ion uptake of cardiac sarcoplasmic reticulum and/or an effect of inhibiting overaccumulation of intracellular calcium ions.

The substances having an effect of improving calcium ion uptake of cardiac sarcoplasmic reticulum of the present invention mean substances having an effect of improving of the reduced sarcoplasmic reticulum calcium-pumping ATPase activity in brief-ischemic/reperfused myocardium in dogs showing the following Reference Examples. The substances are not construed as being limited thereto without departing the scope thereof Namely, when it is studied whether the substance has an effect of improving of the reduced sarcoplasmic reticulum calcium-pumping ATPase activity in brief-ischemic/reperfused myocardium in dogs showing the following Reference Examples or not, if the substance has an effect of improving it, it is determined that the substance has an effect of improving calcium ion uptake of cardiac sarcoplasmic reticulum of the present invention.

The substances having an effect of inhibiting overaccumulation of intracellular calcium ions of the present invention mean substances having an effect of inhibiting the action of isoproterenol showing the following Reference Examples. The substances are not construed as being limited thereto without departing the scope thereof. Namely, when it is studied whether the substance has an effect of inhibiting the action of isoproterenol showing the following Reference Examples or not, if the substance has an effect of inhibiting it, it is determined that the substance has an effect of inhibiting over-accumulation of intracellular calcium ions of the present invention.

The examples of the above substances include an aminobenzenesulfonic acid derivative or salt, or hydrate or solvate thereof, represented by the above formula (I).

In the above formula (I), $C_1$-$C_6$ alkyl group as $R_1$ include such as methyl, ethyl, propyl, iso-propyl, butyl, iso-butyl, sec-butyl, tert-butyl, pentyl, iso-pentyl, neo-pentyl, tert-pentyl, hexyl and n-hexyl groups. $C_3$-$C_7$ cycloalkyl group include such as cyclopropyl, cyclobutyl, cyclopentyl, cyclohexyl and cycloheptyl groups. $C_1$-$C_4$ halogenated alkyl group include such as trifluoromethyl, trifluoroethyl and pentafluoroethyl groups. Halogen atom include such as fluorine, chlorine and bromine atoms. $C_6$-$C_{12}$ aryl group include such as phenyl and naphthyl groups.

As preferable examples, $R_1$ include hydrogen atom, $C_1$-$C_6$ alkyl group, $C_5$-$C_6$ cycloalkyl group, trifluoromethyl group, halogen atom and phenyl group. As more preferable examples, $R_1$ include $C_1$-$C_3$ alkyl group, cyclohexyl group, trifluoromethyl group, chlorine atom, bromine atom and phenyl group. As most preferable examples, $R_1$ include methyl and propyl groups.

$C_1$-$C_6$ alkyl group as $R_2$ include such as the same as that of $R_1$. $C_7$-$C_{12}$ aralkyl group include such as benzyl, phenethyl and naphthylmethyl groups, which may also have at least one substituent selected from cyano groups, nitro groups, $C_1$-$C_6$ alkoxy groups such as methoxy, ethoxy, propoxy, isopropoxy, butoxy, isobutoxy, tert-butoxy, pentyloxy, isopentyloxy, tert-pentyloxy and hexyloxy groups, halogen atoms such as the same as that of $R_1$, $C_1$-$C_6$ alkyl groups such as the same as that of $R_1$ and amino groups.

As preferable examples, $R_2$ include hydrogen atom, $C_1$-$C_3$ alkyl group and $C_7$-$C_{12}$ aralkyl group which may also have at least one substituent selected from $C_1$-$C_3$ alkoxy groups, $C_1$-$C_3$ alkyl groups and halogen atoms. As more preferable examples, $R_2$ include hydrogen atom and $C_7$-$C_{12}$ aralkyl group which may also have at least one substituent selected from $C_1$-$C_3$ alkoxy groups. As most preferable examples, $R_2$ include hydrogen atom.

As preferable examples in the above formula (I), n represents 2.

As preferable specific compounds of the present invention, for example, those set forth in the following Table 1 and Table 2 may be included.

TABLE 1

| Compound No. | Substitution position of $R_1$ | $R_1$ | N | $R_2$ |
|---|---|---|---|---|
| 1 | — | H | 2 | H |
| 2 | 3 | —CH$_3$ | 2 | H |
| 3 | 3 | —CH$_2$CH$_3$ | 2 | H |
| 4 | 3 | —CH$_2$CH$_2$CH$_3$ | 2 | H |
| 5 | 3 | —CH(CH$_3$)$_2$ | 2 | H |
| 6 | 3 | —(CH$_2$)$_3$CH$_3$ | 2 | H |
| 7 | 4 | —CH$_3$ | 2 | H |
| 8 | 4 | —CH$_2$CH$_3$ | 2 | H |
| 9 | 4 | —(CH$_2$)$_2$CH$_3$ | 2 | H |
| 10 | 4 | —CH(CH$_3$)$_2$ | 2 | H |
| 11 | 4 | —(CH$_2$)$_3$CH$_3$ | 2 | H |
| 12 | 5 | —CH$_3$ | 2 | H |
| 13 | 5 | —CH$_2$CH$_3$ | 2 | H |
| 14 | 5 | —(CH$_2$)$_2$CH$_3$ | 2 | H |
| 15 | 5 | —CH(CH$_3$)$_2$ | 2 | H |
| 16 | 5 | —(CH$_2$)$_3$CH$_3$ | 2 | H |
| 17 | 5 | —(CH$_2$)$_4$CH$_3$ | 2 | H |
| 18 | 5 | —(CH$_2$)$_5$CH$_3$ | 2 | H |
| 19 | 6 | —CH$_3$ | 2 | H |
| 20 | 6 | —CH$_2$CH$_3$ | 2 | H |
| 21 | 6 | —(CH$_2$)$_2$CH$_3$ | 2 | H |
| 22 | — | H | 2 | —CH$_3$ |
| 23 | 3 | —CH$_2$CH$_3$ | 2 | —CH$_3$ |
| 24 | 3 | —(CH$_2$)$_2$CH$_3$ | 2 | —CH$_3$ |
| 25 | 3 | —CH(CH$_3$)$_2$ | 2 | —CH$_3$ |
| 26 | 3 | —(CH$_2$)$_3$CH$_3$ | 2 | —CH$_3$ |
| 27 | 4 | —CH$_3$ | 2 | —CH$_3$ |
| 28 | 4 | —CH$_2$CH$_3$ | 2 | —CH$_3$ |
| 29 | 4 | —(CH$_2$)$_2$CH$_3$ | 2 | —CH$_3$ |
| 30 | 5 | —CH$_3$ | 2 | —CH$_3$ |
| 31 | 5 | —CH$_2$CH$_3$ | 2 | —CH$_3$ |
| 32 | 5 | —(CH$_2$)$_2$CH$_3$ | 2 | —CH$_3$ |
| 33 | 5 | —CH(CH$_3$)$_2$ | 2 | —CH$_3$ |
| 34 | 5 | —(CH$_2$)$_3$CH$_3$ | 2 | —CH$_3$ |
| 35 | 5 | —(CH$_2$)$_4$CH$_3$ | 2 | —CH$_3$ |
| 36 | 5 | —(CH$_2$)$_5$CH$_3$ | 2 | —CH$_3$ |

TABLE 1-continued

| Compound No. | Substitution position of $R_1$ | $R_1$ | N | $R_2$ |
|---|---|---|---|---|
| 37 | 6 | —$CH_3$ | 2 | —$CH_3$ |
| 38 | 6 | —$CH_2CH_3$ | 2 | —$CH_3$ |
| 39 | 6 | —$(CH_2)_2CH_3$ | 2 | —$CH_3$ |
| 40 | 6 | —$CH(CH_3)_2$ | 2 | —$CH_3$ |
| 41 | 6 | —$(CH_2)_3CH_3$ | 2 | —$CH_3$ |
| 42 | 3 | —$(CH_2)_2CH_3$ | 2 | —$(CH_2)_2CH_3$ |
| 43 | 4 | —$(CH_2)_2CH_3$ | 2 | —$(CH_2)_2CH_3$ |
| 44 | 5 | —$CH_3$ | 2 | —$(CH_2)_2CH_3$ |
| 45 | 5 | —$CH_2CH_3$ | 2 | —$(CH_2)_2CH_3$ |
| 46 | 5 | —$(CH_2)_2CH_3$ | 2 | —$(CH_2)_2CH_3$ |
| 47 | 5 | —$CH(CH_3)_2$ | 2 | —$(CH_2)_2CH_3$ |
| 48 | 5 | —$(CH_2)_3CH_3$ | 2 | —$(CH_2)_2CH_3$ |
| 49 | 5 | —$(CH_2)_5CH_3$ | 2 | —$(CH_2)_2CH_3$ |
| 50 | — | H | 2 | —$(CH_2)_2CH_3$ |
| 51 | — | H | 2 |  |
| 52 | 3 | —$CH_3$ | 2 |  |
| 53 | 3 | —$(CH_2)_2CH_3$ | 2 |  |
| 54 | 4 | —$CH_3$ | 2 |  |
| 55 | 4 | —$(CH_2)_2CH_3$ | 2 |  |
| 56 | 5 | —$CH_3$ | 2 | Same as above |
| 57 | 5 | —$CH_2CH_3$ | 2 | Same as above |
| 58 | 5 | —$(CH_2)_2CH_3$ | 2 | Same as above |
| 59 | 5 | —$CH(CH_3)_2$ | 2 | Same as above |
| 60 | 5 | —$(CH_2)_3CH_3$ | 2 | Same as above |
| 61 | 5 | —$(CH_2)_4CH_3$ | 2 |  |
| 62 | 5 | —$(CH_2)_2CH_3$ | 2 |  |
| 63 | 5 | —$CH(CH_3)_2$ | 2 |  |

TABLE 1-continued

Structure: R1-substituted benzene with SO3H at position 1, and at position 2 a piperazine ring N—(CH2)n—N—R2

| Compound No. | Substitution position of R₁ | R₁ | N | R₂ |
|---|---|---|---|---|
| 64 | 5 | —CH(CH₃)₂ | 2 | —CH₂—(2-methoxyphenyl) |
| 65 | 4 | —(CH₂)₂CH₃ | 2 | —(CH₂)₄—(3,4-dimethoxyphenyl) |
| 66 | 5 | —(CH₂)₂CH₃ | 2 | —CH₂—(3,4-dimethoxyphenyl) |
| 67 | 5 | —CH(CH₃)₂ | 2 | —(CH₂)₃—(3,4-dimethoxyphenyl) |
| 68 | 6 | —(CH₂)₂CH₃ | 2 | —CH₂—(3,4-dimethoxyphenyl) |
| 69 | 5 | —(CH₂)₂CH₂ | 2 | —CH₂—(3,4,5-trimethoxyphenyl with additional OCH₃) |
| 70 | 6 | —(CH₂)₂CH₃ | 2 | Same as above |
| 71 | 3 | —(CH₂)₂CH₃ | 2 | —CH₂—(4-methylphenyl) |
| 72 | 4 | —(CH₂)₂CH₃ | 2 | —(CH₂)₃—(4-methylphenyl) |
| 73 | 5 | —(CH₂)₂CH₃ | 2 | —CH₂—(4-methylphenyl) |
| 74 | 6 | —CH(CH₃)₂ | 2 | —CH₂—(4-methylphenyl) |

TABLE 1-continued

| Compound No. | Substitution position of R₁ | R₁ | N | R₂ |
|---|---|---|---|---|
| 75 | 3 | —(CH₂)₂CH₃ | 2 | —CH₂—C₆H₄—Cl |
| 76 | 4 | —(CH₂)₂CH₃ | 2 | Same as above |
| 77 | 5 | —(CH₂)₂CH₃ | 2 | Same as above |
| 78 | 6 | —(CH₂)₂CH₃ | 2 | Same as above |
| 79 | 3 | —(CH₂)₂CH₃ | 2 | —CH₂—C₆H₄—OCH₃ |
| 80 | 4 | —(CH₂)₂CH₃ | 2 | Same as above |
| 81 | 5 | —(CH₂)₂CH₃ | 2 | —(CH₂)₃—C₆H₄—OCH₃ |
| 82 | 6 | —(CH₂)₂CH₃ | 2 | —CH₂—C₆H₄—OCH₃ |
| 83 | — | H | 3 | H |
| 84 | 5 | —CH₃ | 3 | Same as above |
| 85 | 5 | —CH₂CH₃ | 3 | Same as above |
| 86 | 5 | —(CH₂)₂CH₃ | 3 | Same as above |
| 87 | 5 | —CH(CH₃)₂ | 3 | Same as above |
| 88 | 5 | —(CH₂)₃CH₃ | 3 | H |
| 89 | 5 | —(CH₂)₂CH₃ | 3 | —CH₃ |
| 90 | 5 | —(CH₂)₂CH₃ | 3 | —C₆H₃(OCH₃)₂ |
| 91 | 5 | —C₆H₅ | 2 | H |
| 92 | 5 | —F | 2 | Same as above |
| 93 | 5 | —Cl | 2 | Same as above |
| 94 | 5 | —Br | 2 | Same as above |
| 95 | 5 | —CF₃ | 2 | Same as above |
| 96 | 5 | —C₆H₁₁ | 2 | H |
| 97 | 5 | —C₅H₉ | 2 | Same as above |
| 98 | 5 | —C₆H₅ | 2 | —CH₃ |
| 99 | 5 | —Cl | 2 | Same as above |

TABLE 1-continued

| Compound No. | Substitution position of R₁ | R₁ | N | R₂ |
|---|---|---|---|---|
| 100 | 5 | —Br | 2 | Same as above |
| 101 | 5 | —CF₃ | 2 | Same as above |
| 102 | 5 |  | 2 | Same as above |
| 103 | 5 |  | 2 | —CH₃ |
| 104 | 5 |  | 2 | —CH₂—<phenyl> |
| 105 | 5 | —Cl | 2 | Same as above |
| 106 | 5 | —Br | 2 | Same as above |
| 107 | 5 | —CF₃ | 2 | Same as above |
| 108 | 5 |  | 2 | Same as above |
| 109 | 5 |  | 2 | Same as above |

TABLE 2

| Compound No. | Substitution position of R₁ | R₁ | N | R₂ |
|---|---|---|---|---|
| 110 | 5 | —CH₂CH₂CH₃ | 2 | H |
| 111 | 5 | —CH(CH₃)₂ | 2 | H |
| 112 | 5 |  | 2 | H |
| 113 | 5 | (phenyl) | 2 | H |
| 114 | 5 | —Cl | 2 | H |
| 115 | 5 | —Br | 2 | H |
| 116 | 5 | —CF₃ | 2 | H |

In the above Table 1 and Table 2, compounds wherein the substitution position of $R_1$ is 5 are preferable. More preferable compounds are as follows:

5-methyl-2-(1-piperazinyl)benzenesulfonic acid;
5-trifluoromethyl-2-(1-piperazinyl)benzenesulfonic acid;
5-n-propyl-2-(1-piperazinyl)benzenesulfonic acid;
5-phenyl-2-(1-piperazinyl)benzenesulfonic acid;
5-chloro-2-(1-piperazinyl)benzenesulfonic acid;
5-bromo-2-(1-piperazinyl)benzenesulfonic acid;
5-iso-propyl-2-(1-piperazinyl)benzenesulfonic acid;
5-cyclohexyl-2-(1-piperazinyl)benzenesulfonic acid;
5-n-propyl-2-(1-homopiperazinyl)benzenesulfonic acid;
5-n-propyl-2-[4-(2,3,4-trimethoxybenzyl)-1-piperazinyl] benzenesulfonic acid; and
5-n-propyl-2-[4-(3,4-dimethoxybenzyl)-1-piperazinyl] benzenesulfonic acid.

In the above compounds, more preferable examples include 5-methyl-2-(1-piperazinyl)benzenesulfonic acid and 5-n-propyl-2-(1-piperazinyl)benzenesulfonic acid.

Also, the pharmaceutically acceptable salts of the above compounds are included within the scope of the present invention.

The above salts are alkali metal salts or alkaline earth metal salts such as sodium salts, potassium salts, magnesium salts, calcium salts and aluminum salts; lower alkylamine salts such as ammonium salts and triethylamine salts; hydroxy lower alkylamine salts such as 2-hydroxyethylamine salts, bis-(2-hydroxyethyl) amine salts, tris-(hydroxymethyl) aminomethane salts and N-methyl-D-glucamine salts; cycloalkylamine salts such as dicyclohexylamine salts; benzylamine salts such as N, N-dibenzylethylenediamine salts and amine salts such as dibenzylamine salts; inorganic acid salts such as hydrochlorides, hydrobromides, sulfates and phosphates; and organic acid salts such as fumarates, succinates and lactates.

Such compounds may be used as salts thereof, in freeform, or hydrates or solvates thereof as the active ingredient in the medicament of the present invention. Solvents which may be used for preparation of the above solvates include, for example, methanol, ethanol, isopropylalchol, acetone, ethyl acetate and methylenechloride.

The most preferable active ingredient of the present invention is 5-methyl-2-(1-piperazinyl)benzenesulfonic acid monohydrate.

Aminobenzenesulfonic acid derivatives represented by the above formula (I) per se are known compounds and can be easily synthesized according to, for example, the method described in Japanese Patent Application Publication Nos. 7263/1991 and 221479/1997, European Patent Application Publication Nos. 390654 and 779283, and U.S. Pat. Nos. 5,053,409 and 5,990,113. These compounds are easily available for those skilled in the art.

The substances having an effect of improving calcium ion uptake of cardiac sarcoplasmic reticulum and/or an effect of inhibiting overaccumulation of intracellular calcium ions have an effect of inhibiting delayed neural cell death due to cerebral ischemia shown in the following Examples. Therefore, there can be used as therapeutic and/or prophylactic agents for disease selected from the group consisting of cerebrovascular disease, traumatic head injury and postencephalitis. The preferable example in cerebrovascular disease is ischemic cerebrovascular diseases such as stroke, subarachnoid hemorrhage, cerebral hemorrhage and cerebral arterial sclerosis. There can be used as the inhibitor for neuronal cell death for disease leading to neuronal deficiency due to cerebral disturbance.

The substances having an effect of improving calcium ion uptake of cardiac sarcoplasmic reticulum and/or an effect of inhibiting overaccumulation of intracellular calcium ions have an effect of inhibiting neuronal cell degeneration due to cerebral ischemia and/or improving hypofunction due to neuronal cell degeneration shown in the following Examples. Therefore, there can be used as therapeutic and/or prophylactic agents for diseases selected from the group consisting of disturbance of intelligence as basic manifestation of dementia (amnesia, disturbance of memorization, disorientation, fugue, etc.) and the symptom accompanied thereof such as delirium including phantasm and hallucination, delusion, aggressive behavior, strain, agitation and hypobulia. Namely, there can be effective for the symptom selected from the group consisting of amnesia, disturbance of memorization, disorientation, fugue, aprosexia, logopathy, hypobulia, emotional instability, delirium, delusion and behavior disorder.

The substances having an effect of improving calcium ion uptake of cardiac sarcoplasmic reticulum and/or an effect of inhibiting overaccumulation of intracellular calcium ions are effective for the therapeutic and/or prophylactic agents for diseases caused by neuronal cell degeneration according to the above efficacy. These neuronal degeneration diseases include Alzheimer's disease, Parkinson's disease, Parkinsonian syndrome, progressive supranuclear pals, subacute sclerosing parencephalitis, dementia pugilistica, Pic's syndrome, corticobasal ganglia degeneration disease, fronttemporal dementia and disturbance of consciousness or dyskinesia caused by head injury.

When the substance having an effect of improving calcium ion uptake of cardiac sarcoplasmic reticulum and/or an effect of inhibiting overaccumulation of intracellular calcium ions of the present invention is used as a therapeutic and/or prophylactic agents for nervous system disorder, it is adapted orally or parenterally to human in conventional manner. As the dosage form for oral administration, there may be included granules, fine granules, powders, tablets, hard capsules, soft capsules, syrups, emulsions, suspensions and solutions. As the dosage form for parenteral administration, injections, suppositories and percutaneous agents, may be included.

The active ingredient of the present invention is contained in the above dosage form together with a solid or liquid carrier for pharmaceutical or an additive for pharmaceutical such as excipient, stabilizer, lubricant, sweetener, preservative and suspending agent, and the ratio of the active ingredient in therapy based on the carrier component should be preferably within the range from 1% by weight to 90% by weight.

Examples of solid carriers to be used may include lactose, kaolin, sucrose, crystalline cellulose, corn starch, talc, agar, pectin, acacia, stearic acid, magnesium stearate, lecithin and sodium chloride. Examples of liquid carriers may include syrup, glycerin, peanut oil, polyvinyl pyrrolidone, olive oil, ethanol, benzyl alcohol, propylene glycol and water.

The dosage of the substance as active ingredient can be determined suitably depending on each substance according to the type of disease to be treated or prevented, symptom of the disease, body-weight, age and sex of the patient. When the compounds represented by the above formula (I) as typical examples are used, generally, such formulation may be orally administered to an adult at about 0.01 mg-1,000 mg per day. Preferably, such dosage may be administered in single to several doses per day.

EXAMPLES

The present invention is described in more detail below by referring to Examples, but the present invention, within its scope, is not limited by the following Examples at all. 5-methyl-2-(1-piperazinyl)benzenesulfonic acid monohydrate used in the following Examples was prepared according to the method described in Example 1 of Japanese Patent Application Publication No. 221479/1997. 5-n-propyl-2-(1-piperazinyl)benzenesulfonic acid used in the following Examples was prepared according to the method described in Example 2 of Japanese Patent Application Publication No. 7263/1991. Compound No. in Reference Example 2 corresponds to Compound No. in Table 1 and Table 2 as mentioned above and these compounds were prepared according to the method described in Japanese Patent Application Publication No. 7263/1991.

Example 1

Action on Delayed Neuronal Cell Death in Rat (1)

Bilateral vertebral arteries of Wister male rats weighing 250 to 300 g were electrically cauterized before 24 hours from ischemic induction to prepare rats showing no neurological symptom such as hemiplegia. Only vertebral arteries of rats were cauterized to prepare rats as sham operation group. Before 30 minutes from ischemic induction, 0.1 mg/kg-b.w. or 1 mg/kg-b.w. of 5-methyl-2-(1-piperazinyl)benzenesulfonic acid monohydrate suspended in distilled water was administered orally to the rat of drug administration group and the equivalent dose of distilled water was administered to the rat of control group.

Ischemia was inducted by 10-minutes' bilateral occlusion of the common carotid arteries under ether anesthesia. Those rats who did not show disappearance of righting reflex during the occlusion were excluded. During ischemia and after recirculation, until recovery of righting reflex, the rats were put on the heating mat to maintain their body temperature. After 72 hours from recirculation, the brain of the rat was fixed by perfusion with a fixative, FAM (formalin:acetic acid:methanol □1:1:8). After that, it was embedded by paraffin and a 5 μm thick slice of the forebrain was prepared in an usual manner Haematoxylin stain was conducted and the number of hippocampus CA1 pyramidal cells were counted to obtain the number of the cells per mm (neuronal density). The number of hippocampus CA1 pyramidal cells in sham operation group was 166.0±6.7. After 10 minutes ischemia induction, the number of hippocampus CA1 pyramidal cells in control group (distilled water administration group) was 31.2±13.3 and about 80% of total neuronal cells were led into degeneration and necrosis. The number of hippocampus CA1 pyramidal cells in 0.1 and 1 mg/kg 5-methyl-2-(1-piperazinyl)benzenesulfonic acid monohydrate oral administration group was 74.3±16.0 and 104.1±21.9, respectively. Both of them inhibited neuronal cell death dose-dependently and there is a significant difference between 1 mg/kg administration group and the control group.

Figure 1:
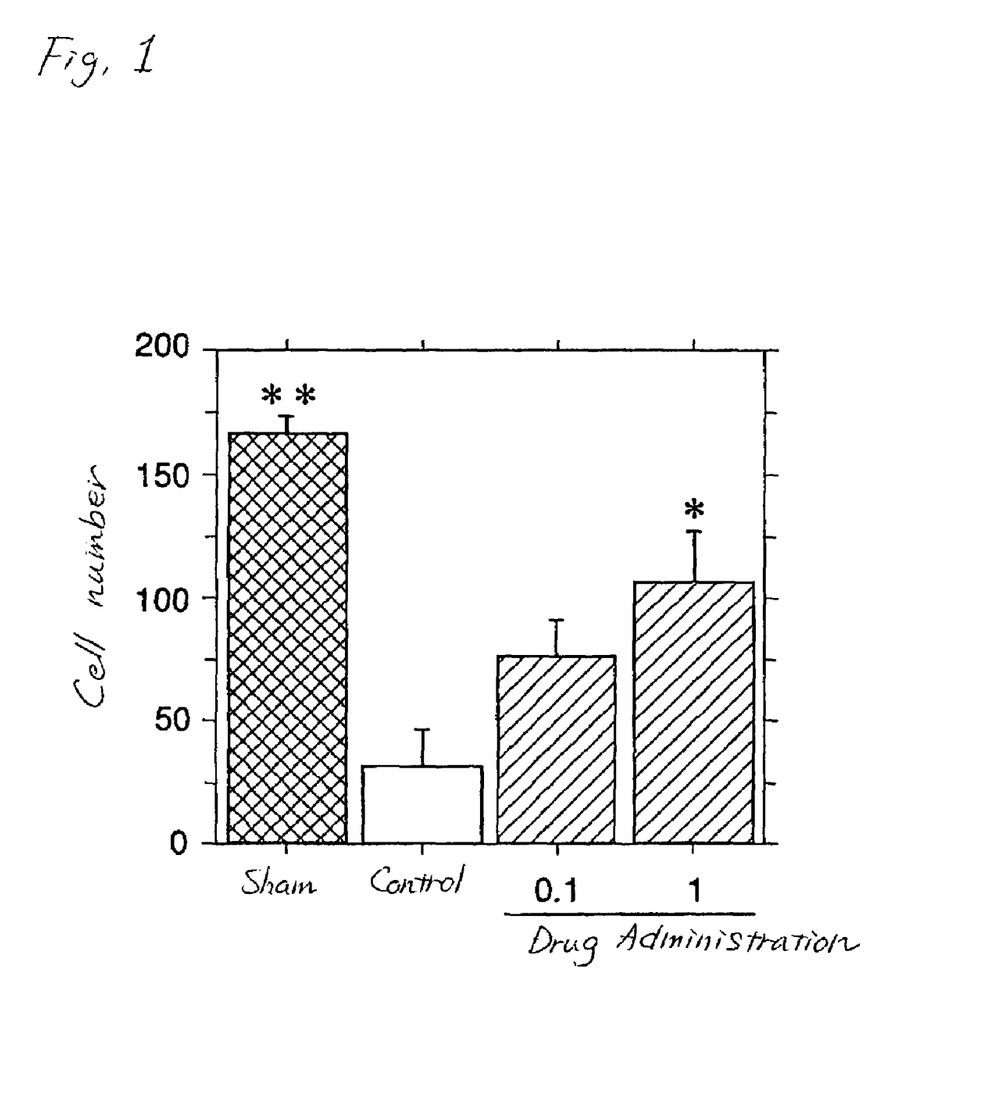
FIG. 1 is a diagram showing the action on delayed neuronal cell death in Example 1, in which the abscissa indicates sham operation group, control group and drug administration group (dose: 0.1, 1 mg/kg). and the ordinate the number of cell per mm.

The results obtained are shown in FIG. 1. 5-methyl-2-(1-piperazinyl)benzenesulfonic acid monohydrate inhibited significantly delayed neuronal cell death. P of the sham operation group was less than 0.01 and that of 1 mg/kg administration group was less than 0.05.

Example 2

Action on Disturbance of Passive Avoidance Behavior in Rat (1)

Bilateral vertebral arteries of Wister male rats weighing 250 to 300 g were electrically cauterized before 48 hours from ischemic induction to prepare rats showing no neurological symptom such as hemiplegia. Only vertebral arteries of rats were cauterized to prepare rats as sham operation group. Before 30 minutes from ischemic induction, 0.1 mg/kg-b.w. or 1 mg/kg-b.w. of 5-methyl-2-(1-piperazinyl)benzenesulfonic acid monohydrate suspended in distilled water was administered orally to the rat of drug administration group and the equivalent dose of distilled water was administered to the rat of control group. The experiment was conducted by using the apparatus consisting of the bright room (50×50×50 cm) with 100 W lamp and the dark room (20×14×20 cm). The rat electrically cauterized bilateral vertebral arteries was put in the bright room to count the transit time to the dark room. The transit time was identified the reaction latency in the acquisition trial.

Those rats who did not show more than 90 seconds transit time were excluded. The guillotine door was closed when the rat entered into the dark room and the rat was given electrical shock (2.9 mA, 5 seconds) from the floor grid to finish the acquisition trial.

Ischemia was inducted by 5-minutes' bilateral occlusion of the common carotid arteries under ether anesthesia. Those rats who did not show disappearance of righting reflex during the occlusion were excluded. During ischemia and after recirculation, until recovery of righting reflex, the rats were put on the heating mat to maintain their body temperature. After 48 hours from recirculation, the retention trial was conducted. As the same manner as the acquisition trial, the rat put in the bright room had been observed for at most 300 seconds to count the transit time to the dark room (the reaction latency). The reaction latency of those rats who did not transit to the dark room after 300 seconds was seemed that the reaction latency was 300 seconds.

Figure 2:
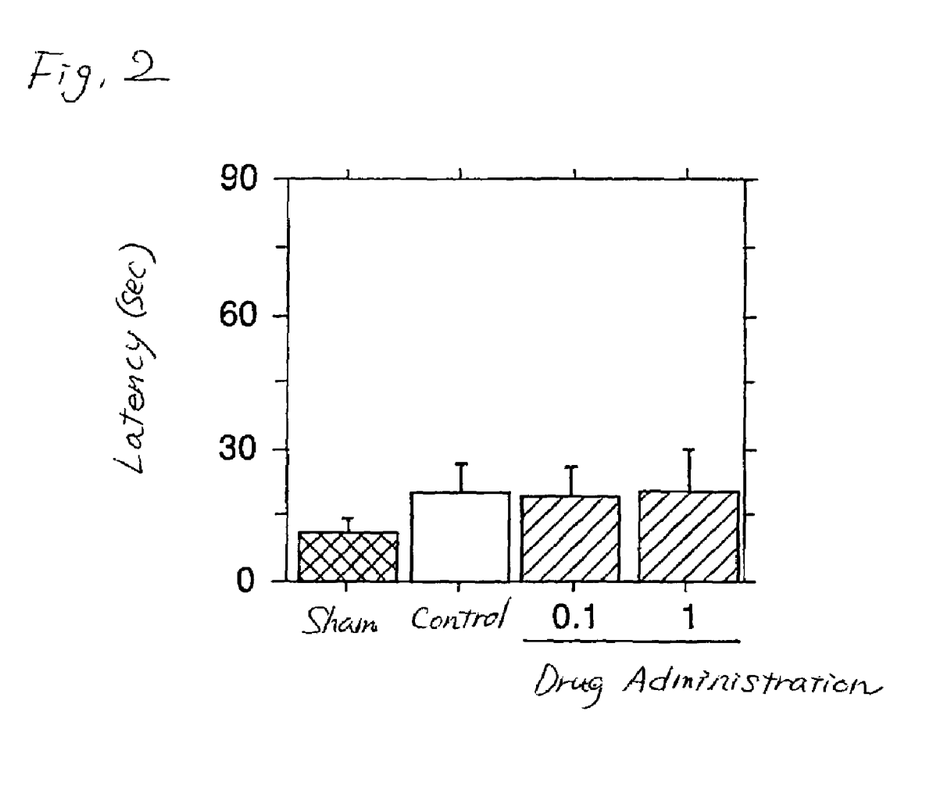
FIG. 2 is a diagram showing the reaction latency in acquisition trial in Example 2, in which the abscissa indicates sham operation group, control group and drug administration group (dose; 0.1, 1 mg/kg), and the ordinate reaction latency (second).
Figure 3:
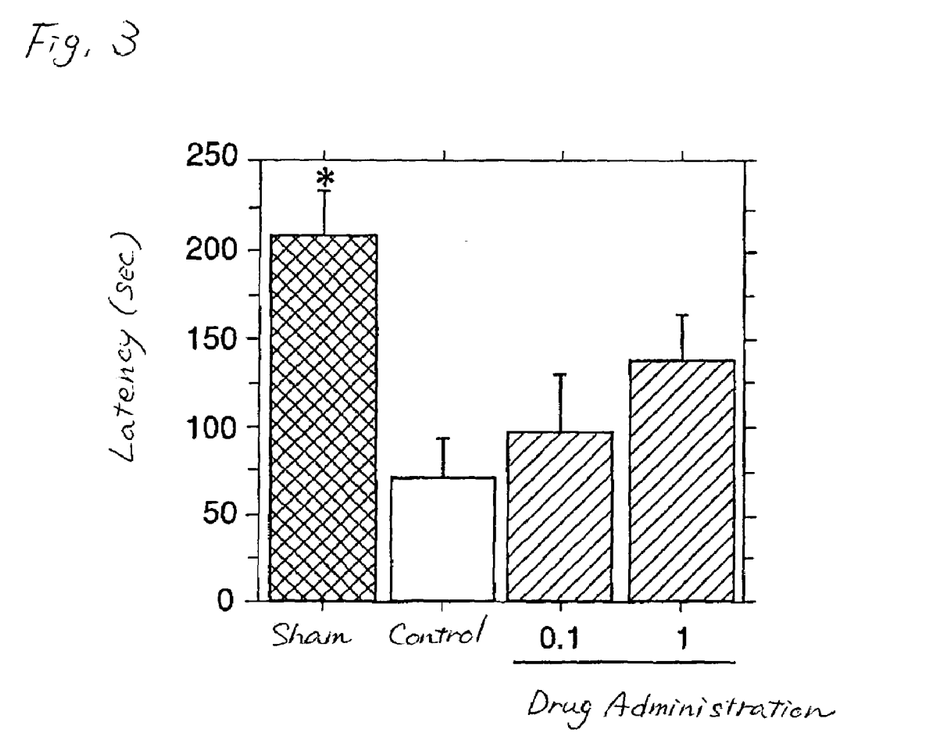
FIG. 3 is a diagram showing the reaction latency in retention trial in Example 2, in which the abscissa and the ordinate indicates the same as those of FIG. 2.

The reaction latency in the retention trial after 5 minutes' ischemic induction was counted. The reaction latency of the sham operation group was 206.1±29.4 seconds and that of the control group (distilled water administration group) was 71.4±29.4 seconds. There is a significant difference between them and disturbance of passive avoidance behavior was observed. The reaction latency of 0.1 and 1 mg/kg 5-methyl-2-(1-piperazinyl)benzenesulfonic acid monohydrate oral administration group was 97.7±31.2 and 139.0±27.5, respectively. Both of them prolonged the reaction latency in the retention trial dose-dependently and the tendency of improving disturbance of passive avoidance behavior was observed. The results obtained are shown in FIGS. 2 and 3.

Example 3

Action on Delayed Neuronal Cell Death in Rat (2)

The action on delayed neuronal cell death in rat was observed by the same method as Example 1 except for intravenously administering 0.03 mg/kg-b.w. or 0.3 mg/kg-b.w. of 5-n-propyl-2-(1-piperazinyl)benzenesulfonic acid suspended in distilled water instead of 5-methyl-2-(1-piperazinyl)benzenesulfonic acid monohydrate as a drug.

The number of hippocampus CA1 pyramidal cells in sham operation group was 177.8±5.3. After 10 minutes from ischemia induction, the number of hippocampus CA1 pyramidal cells in control group (distilled water administration group) was 71.3±10.3 and about 60% of total neuronal cells were led into degeneration and necrosis. The number of hippocampus CA1 pyramidal cells in 0.03 and 0.3 mg/kg 5-n-propyl-2-(1-piperazinyl)benzenesulfonic acid oral administration group was 125.1±5.7 and 131.9±9.9, respectively. Both of them inhibited neuronal cell death significantly.

Figure 4:
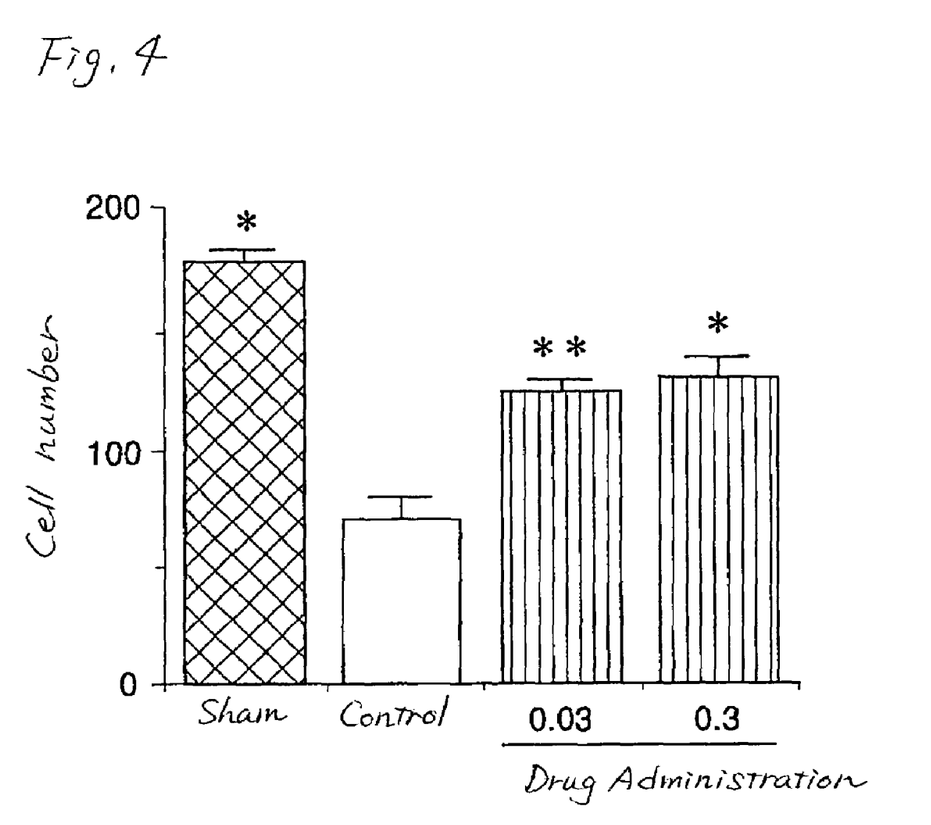
FIG. 4 is a diagram showing the action on delayed neuronal cell death in Example 3, in which the abscissa and the ordinate indicates the same as those of FIG. 1.

The results obtained are shown in FIG. 4. 5-n-propyl-2-(1-piperazinyl)benzenesulfonic acid inhibited significantly delayed neuronal cell death by the dosage of 0.03 and 0.3 mg/kg. P of the sham operation group and 0.3 mg/kg administration group were less than 0.05 and that of 0.03 mg/kg administration group was less than 0.01.

Example 4

Action on Disturbance of Passive Avoidance Behavior in Rat (2)

The action on disturbance of passive avoidance in rat was observed by the same method as Example 1 except for intravenously administering 0.03 mg/kg-b.w. or 0.3 mg/kg-b.w. of 5-n-propyl-2-(1-piperazinyl)benzenesulfonic acid suspended in distilled water instead of 5-methyl-2-(1-piperazinyl)benzenesulfonic acid monohydrate as a drug.

The reaction latency in the acquisition trial of every group was about 20 seconds and there is no significant difference between them. The reaction latency in the retention trial after 5 minutes' ischemic induction was counted. The reaction latency of the sham operation group was 243.5±31.6 seconds and that of the control group (distilled water administration group) was 88.2±18.1 seconds. There is a significant difference between them and disturbance of passive avoidance behavior was observed. The reaction latency of 0.03 and 0.3 mg/kg 5-n-propyl-2- (1-piperazinyl)benzenesulfonic acid intravenous administration group was 253.4±25.6 and 187.2±36.1, respectively. Both of them prolonged the reaction latency in the retention trial significantly and disturbance of passive avoidance behavior was improved.

Figure 5:
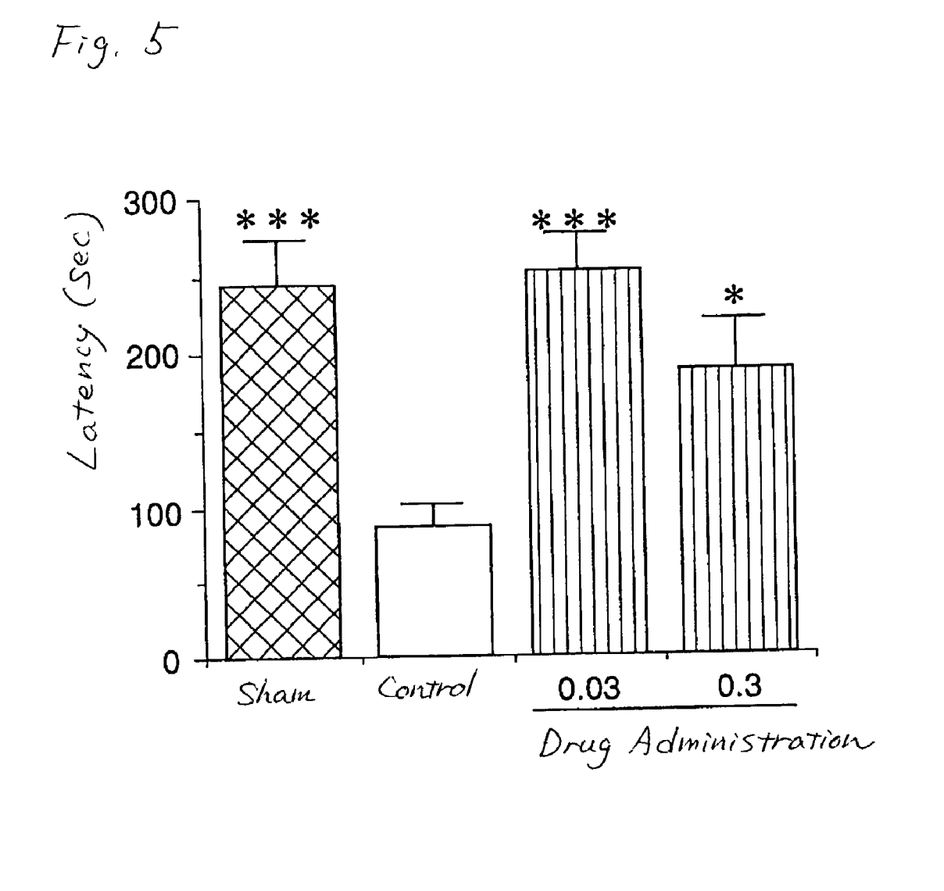
FIG. 5 is a diagram showing the reaction latency in retention trial in Example 4, in which the abscissa and the ordinate indicates the same as those of FIG. 2.

The results obtained are shown in FIG. 5. P of the sham operation group and 0.03 mg/kg administration group were less than 0.001 and that of 0.3 mg/kg administration group was less than 0.05.

Reference Example 1

Effect of Improving Calcium Ion Uptake of Cardiac Sarcoplasmic Reticulum

The chest of mongrel dogs (adults, male and female) was opened under anesthesia with pentobarbital (30 mg/kg, i.v.) and a portion of the left coronary anterior descending (LAD) was dissected. A catheter-tip-pressure transducer (Millar; MPC-500) was inserted from the left carotid artery into the left ventricle to determine the left ventricular pressure and its first differential value (dP/dt). A pair of crystal probes were mounted in the LAD region to determine changes in regional segment length. Diastolic segment length (EDL; threshold point of dP/dt) and systolic segment length (ESL; dP/dt(−) max point) were determined from the waveform of dP/dt, and the regional segment shortening (% SS) in the ischemic/reperfused myocardium was calculated as follows:

$$\% \ SS = (EDL - ESL)/ESL \times 100$$

After hemodynamic stability is established following operation, the dissected portion of LAD was occluded for 30 minutes and then reperfused for 1 hour. At the same time, the cardiac function (% SS) in the above-described ischemic/reperfused region was continuously monitored throughout the protocol.

The animals were randomly grouped into two groups, one consisting of animals to be administered with 5-methyl-2-(1-piperazinyl)benzenesulfonic acid monohydrate (drug administration group; N=6) and the other of control group (N=6). The dogs of drug administration group were intravenously administered with 3 µg/kg of 5-methyl-2-(1-piperazinyl)benzenesulfonic acid monohydrate into the right femoral vein 5 minutes before reperfusion, followed by continuous infusion at the equal amount of saline.

After 1-hour reperfusion, their hearts were isolated and the myocardium in post-ischemic region and non-ischemic region the left ventricles were collected from which the fractions having sarcoplasmic reticulum calcium ion-ATPase activity were extracted to be subjected to protein assay (Bradford method) and stored at −80° C. The defrozen fractions were used to determine calcium ion-ATPase activity. The activity was determined by measuring the amount of the generated inorganic phosphate (Pi) by colorimetry using phosphor/molybdic acid and malachite green (µmoles Pi/mg protein/min).

Figure 6:
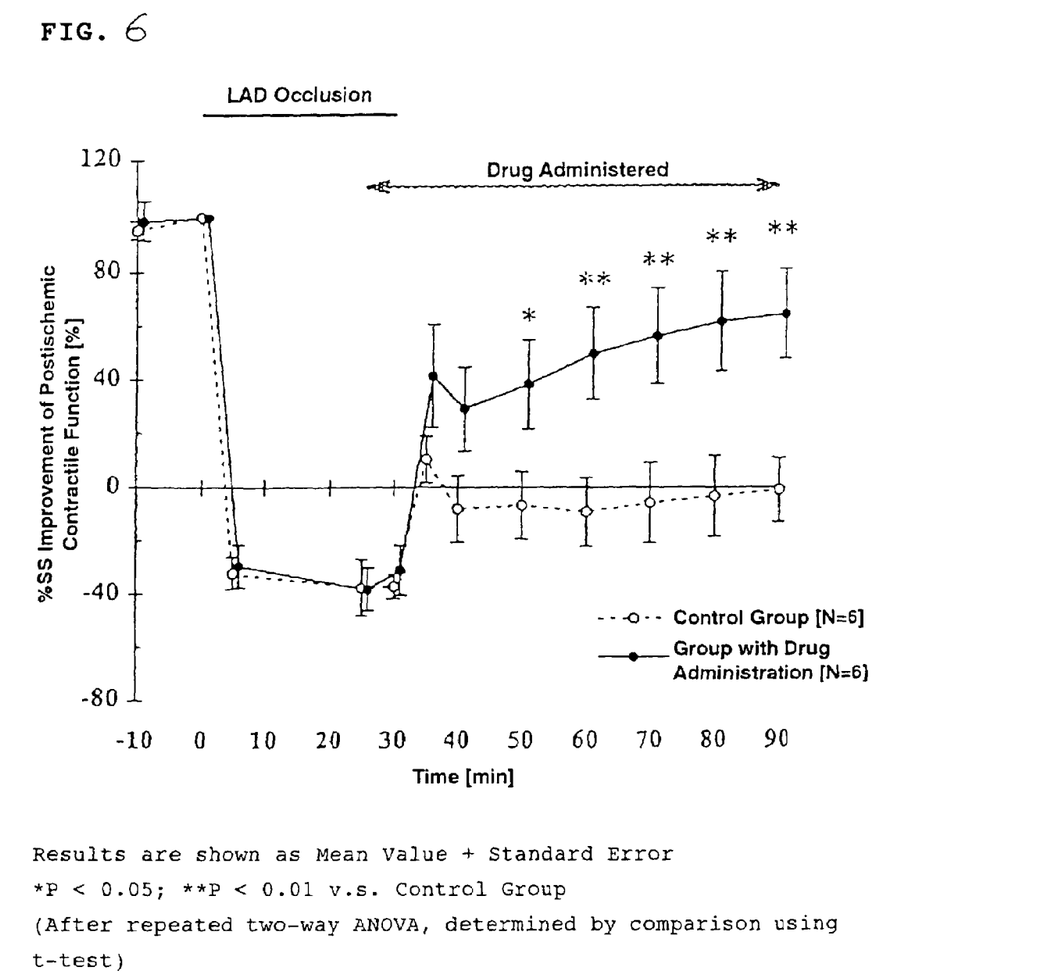
FIG. 6 is a diagram showing the action of improving the regional cardiac function (% SS) in the ischemic/reperfused myocardium in Reference Example 1.

The time-dependent recovery rates of regional cardiac function (% SS) in post-ischemic region relative to pre-ischemic value, for control group and drug administration group are shown in FIG. 6. Contractile function of myocardium after 30 minute-LAD occlusion followed by reperfusion was significantly reduced. Particularly, the reduced state was maintained for 1 hour in the control group. In drug administration group, regional cardiac function in post-reperfusion region was significantly improved when compared to that of the control group (time-course recovery rate for each group was analyzed by repeated two-way ANOVA and t-test was carried out at each time point after ischemia when a significant difference was present). Thus, it was demonstrated that the reduced cardiac function in the post-ischemic region of the myocardium after reperfusion will be improved by administration of 5-methyl-2-(1-piperazinyl)benzenesulfonic acid monohydrate just prior to reperfusion.

Figure 7:
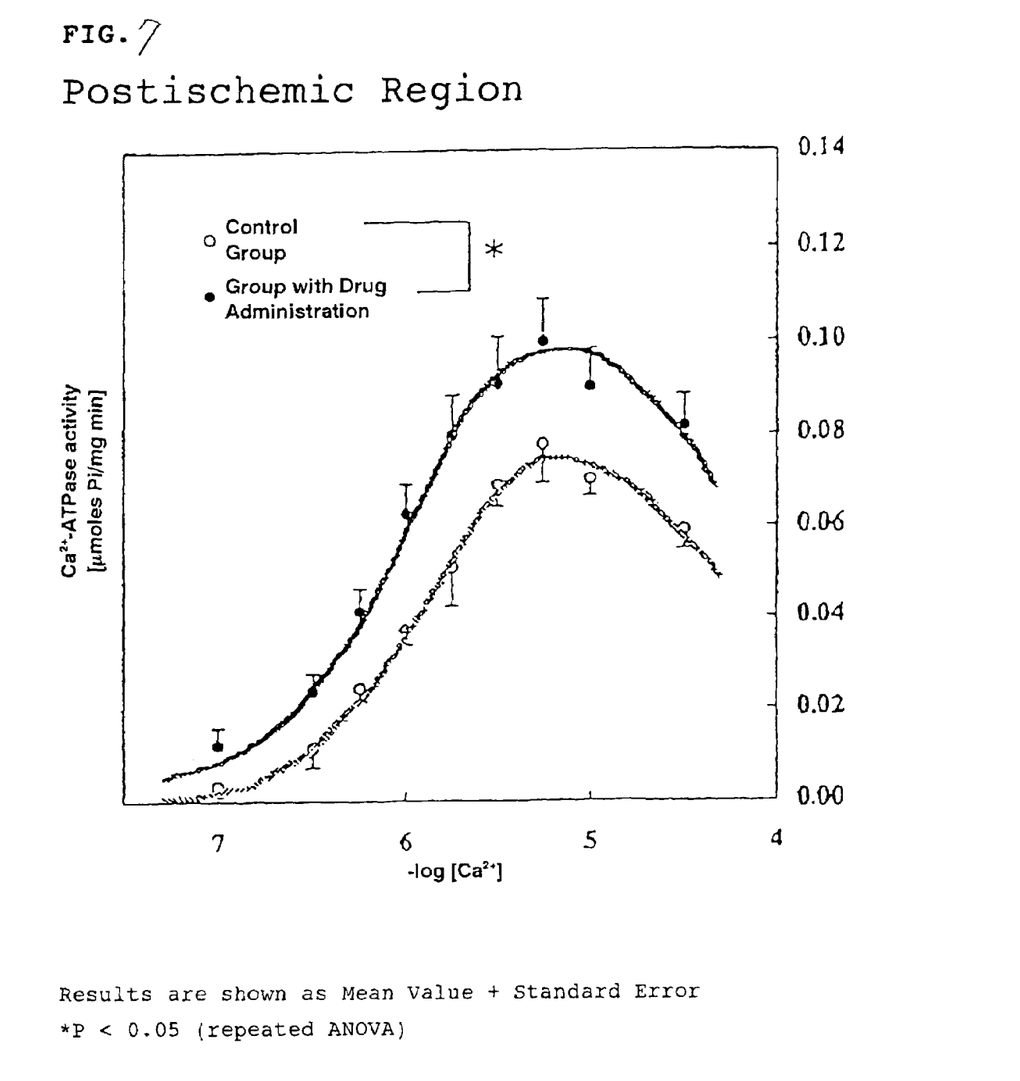
FIG. 7 is a diagram showing the action of improving the reduction in calcium ion uptake ability of the cardiac sarcoplasmic reticulum of the ischemic/reperfused myocardium in vivo in Reference Example 1.
Figure 8:
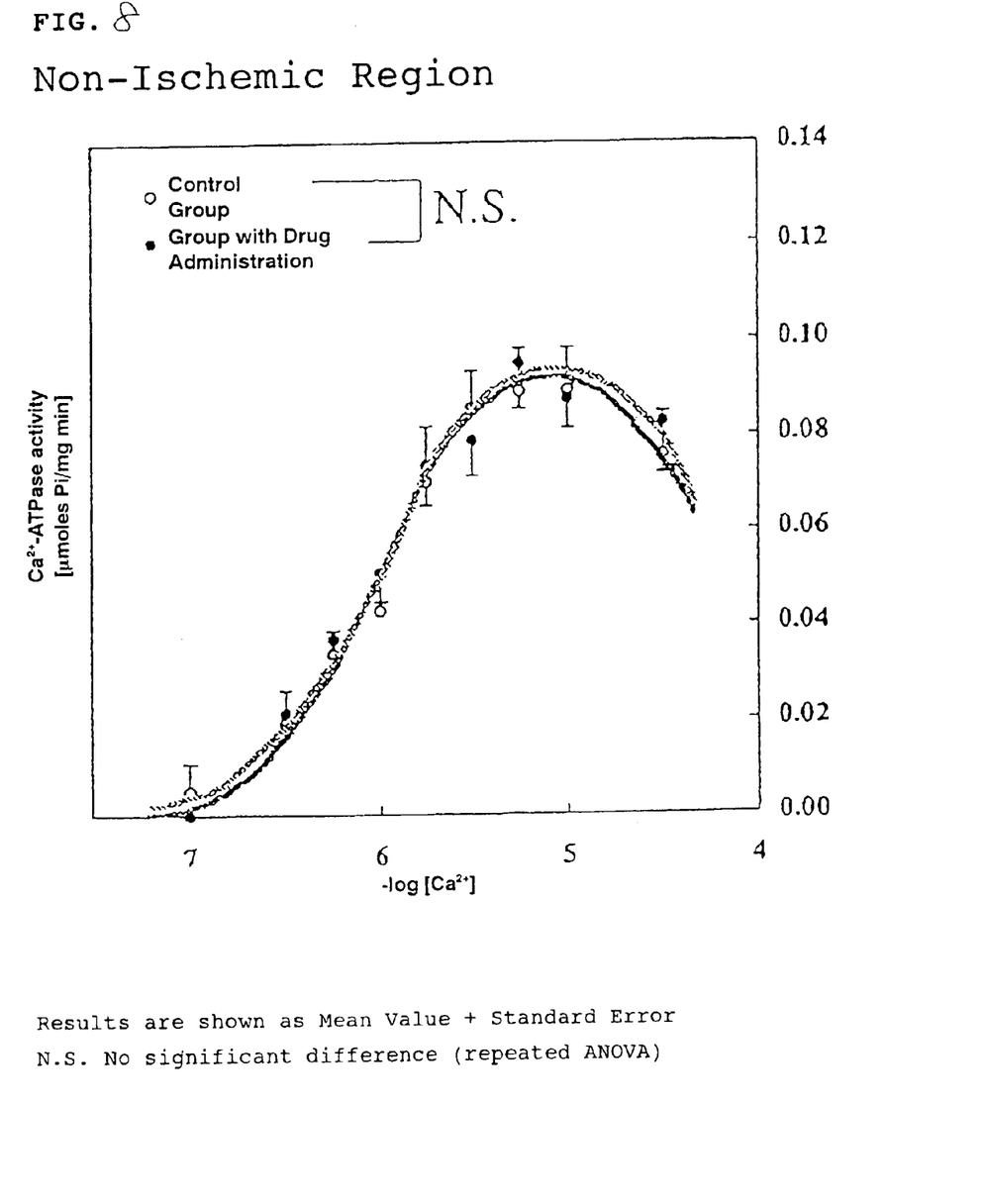
FIG. 8 is a diagram showing the effect on calcium ion uptake ability in non-ischemic region in Reference Example 1.

Next, results obtained from calcium ion-ATPase activity assay of the sarcoplasmic reticulum collected from each region are shown in FIGS. 7 and 8. The calcium ion-ATPase activity of the sarcoplasmic reticulum showed calcium ion-concentration-dependent patterns; the activity was increased at the threshold of 0.1 µM of calcium ion concentration and reached to the peak at about 10 µM. The ATPase activity was proved to be derived from the sarcoplasmic reticulum since the activity was completely inhibited by Thapsigargin (1 µM) which is known to be a specific inhibitor of the sarcoplasmic reticulum calcium ion-ATPase.

In control group which was administered with saline, sarcoplasmic reticulum calcium-ATPase activity of the myocardium collected from post-ischemic region was about 79% ($[Ca^{2+}]$=10 µM) of that of non-ischemic region.

Next, the activity was compared between the control group and drug administration group for each of post-ischemic region and non-ischemic region. In the post-ischemic region, calcium ion-ATPase activity of the drug administration group was significantly higher than that of the control group (P<0.05 by repeated two-way ANOVA). For example, their activities at calcium ion concentration of 10 µM were 0.090±0.008 vs 0.070±0.004 [µmol Pi/mg min], respectively. Thus, it was proved that the reduced sarcoplasmic reticulum calcium ion uptake ability caused by ischemia and reperfusion is significantly improved by administering 5-methyl-2-(1-piperazinyl)benzenesulfonic acid monohydrate just prior to reperfusion.

Further, the calcium ion-ATPase activity of sarcoplasmic reticulum from non-ischemic region was similarly compared between the two groups. The results showed no significant difference between the control group and drug administration group. For example, there was little difference between the two groups in the activity at calcium ion concentration of 10 µM (drug administration group: 0.088±0.006; control group: 0.089±0.009 [µmol Pi/mg min]).

The above results indicated that 5-methyl-2-(1-piperazinyl)benzenesulfonic acid monohydrate may improve the reaction in sarcoplasmic reticulum calcium ion-ATPase activity induced by ischemia/reperfusion while it has little effect on the ATPase activity in non-ischemic region. Further, 5-methyl-2-(1-piperazinyl)benzenesulfonic acid monohydrate improved reduced cardiac function in ischemia-reperfusion region as well. Thus, 5-methyl-2-(1-piperazinyl)benzenesulfonic acid monohydrate was proved to improve abnormal sarcoplasmic reticulum calcium ion uptake in the post-ischemic myocardium, as well as post-ischemic reduction in cardiac function.

Reference Example 2

Effect of Inhibiting Overaccumulation of Intracellular Calcium Ions

For the evaluation of the extent of inhibiting overaccumulation of intracellular calcium ions, inhibition of the cardiotonic action of isoproterenol by the compounds described in Table 1 and Table 2 as mentioned above was measured.

That is to say, since isoproterenol has been known to cause calcium ions overload by excessive calcium ions influx into cardiac myocytes (Fleckenstein A., Janke J., Doring H., Leder O.; Recent advances in Studies on cardiac structure and metabolism, Myocardial Biology, Vol. 4, pp. 563-580

(1974)), the compounds which inhibit the action of isoproterenol can inhibit intracellular calcium ions overload.

(Method)

The papillary muscle of the right ventricle isolated from male Hartley guinea-pigs (body weight: 250 to 350 g) was suspended in an organ bath filled with a nutrient solution (Krebs-Henseleit solution). The temperature of the nutrient solution was maintained at 32° C., and the solution was aerated with a gas mixture of 95% oxygen and 5% carbon dioxide. The papillary muscle was applied with a resting tension of about 0.5 g, and stimulated with platinum electrodes by a rectangular pulse of a duration of 1 msec, a frequency of 1 Hz and a voltage higher by 15% than the threshold value. The developed tension of the papillary muscle was measured through a tension transducer and recorded with a polygraph system. After the preparation was stabilized for about 90 minutes, isoproterenol ( $10^{-3}$ to $10^{-7}$ M) was added into the organ bath so that developed tension could be increased by 100% or more, and at the point when the maximum response was obtained, the compounds of the present invention were added into the organ bath, and % inhibition of the developed tension increased by isoproterenol was measured.

(Results)

The % inhibition of the compounds are shown in Table 3. As shown in Table 3 above, it is apparent that the drugs according to the present invention can inhibit the action of isoproterenol since they inhibit increase in myocardial contractility by isoproterenol. Accordingly, it can be understood that the drugs according to the present invention can inhibit intracellular calcium ions overload.

TABLE 3

| Compound No. | Inhibition (%) Drug concentration (M) | | |
|---|---|---|---|
| | $10^{-5}$ | $10^{-4}$ | $10^{-3}$ |
| 12 | — | — | 18.5 |
| 14 | 10.4 | 19.2 | — |
| 66 | — | — | 52.4 |
| 69 | — | — | 21.4 |
| 91 | — | — | 17.2 |
| 93 | — | — | 28.0 |

TABLE 3-continued

| Compound No. | Inhibition (%) Drug concentration (M) | | |
|---|---|---|---|
| | $10^{-5}$ | $10^{-4}$ | $10^{-3}$ |
| 94 | — | — | 18.5 |
| 110 | 12.5 | 18.2 | 42.9 |
| 111 | — | — | 27.5 |

INDUSTRIAL APPLICABILITY

The medicament comprising as the active ingredient substances having an effect of improving calcium ion uptake of cardiac sarcoplasmic reticulum and/or an effect of inhibiting overaccumulation of intracellular calcium ions of the present invention can be used as the therapeutic and/or prophylactic agent for disease selected from the group consisting of cerebrovascular disease, traumatic head injury and postencephalitis, especially, ischemic cerebrovascular disease because of its effect of inhibiting neuronal cell death. Furthermore, the medicament of the present invention can be used as the therapeutic and/or prophylactic agent for disease selected from the group consisting of dementia and neuronal degeneration disease because of its effect of inhibiting neuronal degeneration due to cerebral ischemia and improving disorder of memory.

This application was filed as priority of Japanese Patent Application Nos. 362680/1999 and 65272/2000.

The invention claimed is:

1. A method of decreasing neuronal cell death in a patient with ischemic cerebrovascular disease selected from the group consisting of subarachnoid hemorrhage and cerebral hemorrhage, which comprises administering a pharmaceutical composition comprising a compound selected from the group consisting of 5-methyl-2-(1-piperazinyl) benzenesulfonic acid, 5-n-propyl-2-(1-piperazinyl) benzenesulfonic acid, and a salt, hydrate or solvate thereof, to a patient in need thereof.

2. The method according to claim 1, wherein the compound is 5-methyl-2-(1-piperazinyl)benzenesulfonic acid monohydrate.

* * * * *